(12) United States Patent
Roig

(10) Patent No.: US 6,849,277 B2
(45) Date of Patent: Feb. 1, 2005

(54) COMPOSITION FOR MOIST SKIN

(76) Inventor: Juan Carlos Roig, 11870 Leeth Ct., West Palm Beach, FL (US) 33142

( * ) Notice: Subject to any disclaimer, the term of this patent is extended or adjusted under 35 U.S.C. 154(b) by 153 days.

(21) Appl. No.: 10/214,637

(22) Filed: Aug. 8, 2002

(65) Prior Publication Data

US 2003/0068351 A1 Apr. 10, 2003

Related U.S. Application Data

(60) Provisional application No. 60/328,143, filed on Oct. 9, 2001.

(51) Int. Cl.[7] .............................................. A61K 31/315
(52) U.S. Cl. ........................ 424/642; 514/865; 514/887
(58) Field of Search ................................ 424/642, 401; 514/887, 865, 886

(56) References Cited

U.S. PATENT DOCUMENTS

| | | |
|---|---|---|
| 4,253,460 A | 3/1981 | Chen |
| 4,341,207 A | 7/1982 | Steer |
| 4,538,603 A | 9/1985 | Pawelchak |
| 4,773,408 A | 9/1988 | Cilento |
| 6,060,079 A | 5/2000 | Freeman |

*Primary Examiner*—Jyothsna Venkat
(74) *Attorney, Agent, or Firm*—Alvin S. Blum

(57) ABSTRACT

The invention is a composition and method for prophylactic or therapeutic treating skin that is exposed to excessive amounts of moisture. The composition is an ointment or paste that includes zinc oxide, a fungicide, a bactericide, and water-absorbing macromolecular materials in a water-immiscible vehicle. The composition is adherent to the skin. The method of use includes cleaning and drying the skin, and then applying the composition to the skin. A topical anesthetic may be included as well.

6 Claims, No Drawings

COMPOSITION FOR MOIST SKIN

Applicant claims priority based upon provisional patent application Ser. No. 60/328,143 filed on Oct. 9, 2001 incorporated herein by reference.

This invention relates to methods and compositions for treatment of skin that is subjected to conditions of excess moisture.

BACKGROUND OF THE INVENTION

The normal human skin is able to maintain itself and respond well to injury under dry conditions. However, when exposed to excessive moisture for prolonged periods, the skin is more likely to be subject to irritation, inflammation, and infection. Frequent washing, drying, and application of moisture absorbing powders may offer some relief. The skin of the feet is frequently exposed to excessive moisture from perspiration through an entire day. In certain cases this can lead to itching, offensive odor, and persistent fungal infections of skin and nail. Baby bottom skin is subjected to an unnatural moist environment exacerbated by a wet diaper and a plastic cover. Ammonia generated by bacterial action on urine leads to reactive dermatitis. The persistent rashes and inflammation are difficult to treat in the moist environment.

SUMMARY OF THE INVENTION

It is accordingly an object of the invention to provide a composition that can be beneficially applied to skin areas that are subjected to excessive amounts of moisture, and that will remain in place for an extended period of time without being washed away by aqueous fluids. It is another object of the invention that the composition will prevent and relieve the deleterious effects resulting from persistent exposure to excessive moisture. It is another object of the invention to provide a method of treating skin with the composition. The composition creates a moisture absorbing barrier that enables the healing components of the composition and the normal healing processes of the skin to act. The healing components include agents to treat or prevent infection.

The composition includes water-absorbing material, zinc oxide for healing, bactericide and fungicide to combat infectious organisms, all distributed in a water-immiscible vehicle in a form suitable for coating the skin surface, such as a paste or ointment to form a moisture absorbing barrier that is adherent to moist skin that does not easily wash away. A topical anesthetic agent may also be incorporated to relieve pain and itching.

These and other objects, features, and advantages of the invention will become more apparent when the detailed description is studied.

DETAILED DESCRIPTION OF PREFERRED EMBODIMENTS

The composition comprises:

Zinc oxide, USP that may be procured in powder form being at least one percent of the composition or already dispersed in mineral oil or petrolatum or the like as an ointment or cream for convenience of handling, making up between 5 and 15 percent of the composition;

A therapeutic amount of one or more fungicides such as, but not limited to, mycostatin powder;

A therapeutic amount of one or more bactericides such as, but not limited to, bacitracin cream;

Water absorbing macromolecular materials or hydrocolloids such as, but not limited to, pectin, gelatin, a salt of carboxymethylcellulose such as sodium carboxymethlcellulose, guar gum, and locust bean gum, making up at least five percent of the composition; and The above components uniformly dispersed in a water-immiscible vehicle such as, but not limited to, petrolatum and mineral oil to provide a water resistant form that is readily applied to the skin, is very adherent to the skin surface, and is not easily washed away.

The composition may optionally contain a topical anesthetic such as, but not limited to, xylocaine jelly to reduce pain and itching.

Typical formulations that have been found to be successful are as follows:

EXAMPLE 1

20 grams of a dry powder mixture of approximately equal parts of pectin, gelatin, and sodium carboxymethlycellulose is combined with 15 grams of zinc oxide cream. 15 grams of bacitracin cream (500 units/gram) is added. 10 grams mycostatin powder (10,000 units/gram) is added The above materials are thoroughly mixed with 75 grams of patrolatum to form a smooth paste that is easily applied to the skin surface. The mixture may be thinned by replacing some of the petrolatum with mineral oil to achieve the desired consistency.

EXAMPLE 2

20 grams of a dry powder mixture of approximately equal parts of powdered pectin, gelatin, and sodium carboxymethlycellulose is combined with 15 grams of zinc oxide cream. 15 grams of bacitracin cream (500 units/gram) is added. 10 grams mycostatin powder (10,000 units/gram) is added. 2 grams of xylocaine jelly (2%) is added. The above materials are thoroughly mixed with 75 grams of patrolatum to form a smooth paste that is easily applied to the skin surface. The mixture may be thinned by replacing some of the petrolatum with mineral oil to achieve the desired consistency.

When examples 1 and 2 have been applied to babies bottoms, there has been a rapid recovery of the skin from rash and inflammation. When these have been applied to the feet, there has been a rapid recovery from fungal infection. Example 2 with the topical anesthetic provides more prompt relief from discomfort.

The method of the invention for treating skin that is exposed to excessive moisture comprises the steps of:

i) providing a composition comprising:
   a) between five and fifteen percent by weight zinc oxide cream;
   b) a therapeutic amount of fungicide;
   c) a therapeutic amount of bactericide;
   d) between five and twenty five percent by weight of water-absorbing macromolecular material; and
   e) the components a), b), c), and d) dispersed in a water-immiscible vehicle adapted for skin application;

ii) cleaning and drying the skin; and iii) applying the composition to the affected skin.

While I have shown and described the preferred embodiments of my invention, it will be understood that the invention may be embodied otherwise than as herein specifically described, and that certain changes in components and the specific manner of practicing the invention may be made within the underlying idea or principles of the invention.

What is claimed is:

1. A method of treating skin that is exposed to excessive moisture comprising the steps of:
   i) providing a composition comprising:
      a) between five and fifteen percent by weight zinc oxide cream;
      b) a therapeutic amount of mycostatin;
      c) a therapeutic amount of bacitracin;
      d) between five and twenty five percent by weight of water-absorbing macromolecular material comprising gelatin, pectin, and a salt of carboxymethlycellulose; and
      e) the components a), b), c), and d) dispersed in a water-immiscible vehicle adapted for skin application;
   ii) cleaning and drying the skin; and
   iii) applying the composition to the affected skin.

2. The method according to claim 1 in which the vehicle is petrolatum and mineral oil.

3. The method according to claim 1, in which the composition further comprises xylocaine.

4. A composition suitable for application to skin for treating the effects of exposure to excessive moisture, the composition comprising:
   a) at least one percent by weight zinc oxide;
   b) a therapeutic amount of mycostatin fungicide;
   c) a therapeutic amount of bacitracin bactericide;
   d) at least five percent by weight of water-absorbing macromolecular material comprising gelatin, pectin, and a salt of carboxymethylcellulose; and
   e) the components a), b), c), and d) dispersed in a water-immiscible vehicle adapted for skin application.

5. The composition according to claim 4 further comprising xylocaine.

6. The composition according to claim 4 in which the vehicle is petrolatum and mineral oil.

* * * * *